United States Patent [19]
Reynolds et al.

[11] Patent Number: 5,938,666
[45] Date of Patent: Aug. 17, 1999

[54] UMBILICAL CORD CLAMP

[75] Inventors: J. Lawrence Reynolds; Paul M. Kurowski, both of London, Canada

[73] Assignee: University of Western Ontario, London, Canada

[21] Appl. No.: 09/049,065

[22] Filed: Mar. 27, 1998

[51] Int. Cl.⁶ .................................................. A61B 17/122
[52] U.S. Cl. ............................................................ 606/120
[58] Field of Search .................................. 606/120, 157, 606/158; D24/143; 24/300, 301, 302, 459, 461, 485

[56] References Cited

U.S. PATENT DOCUMENTS

| | | | |
|---|---|---|---|
| 3,247,852 | 10/1963 | Schneider | 606/120 |
| 4,716,886 | 1/1988 | Schulman et al. | 606/120 |
| 5,575,795 | 11/1996 | Anderson | 606/157 |
| 5,591,173 | 1/1997 | Schifano | 606/157 |

Primary Examiner—Todd E. Manahan
Assistant Examiner—Eduardo C. Robert
Attorney, Agent, or Firm—Robert P. Stratton; Omar A. Nassif; Arne I. Fors

[57] ABSTRACT

A unitary clamp integrally structured from two U-shaped members respectively disposed one from the other by an interjoining web between proximate arms of each U-shaped member, distal ends of each member having latching means mechanism so as to latch, simultaneously, both U-shaped members into a closed position and the interjoining web sheets spacially disposing each U-shaped member into adjacent closing engagement about an umbilical cord. The web sheets are cut by a pair of scissors to sever the cord and one of the U-shaped clamp members is thus attached to the umbilical cord attached to the abdomen of an infant while the other to the umbilical cord connected to the placenta. On voiding of the placenta, the latter is discarded. When healing of the umbilical cord to the infant is achieved, that clamp member may be removed or discarded.

20 Claims, 3 Drawing Sheets

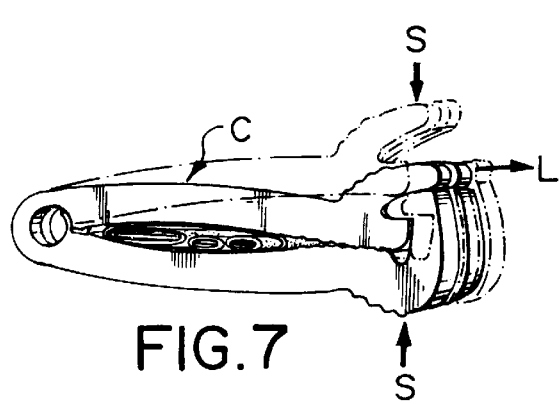
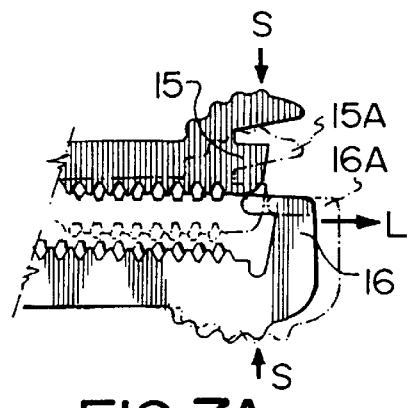
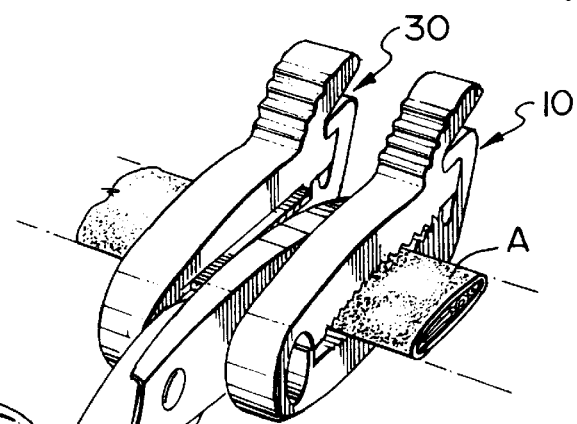
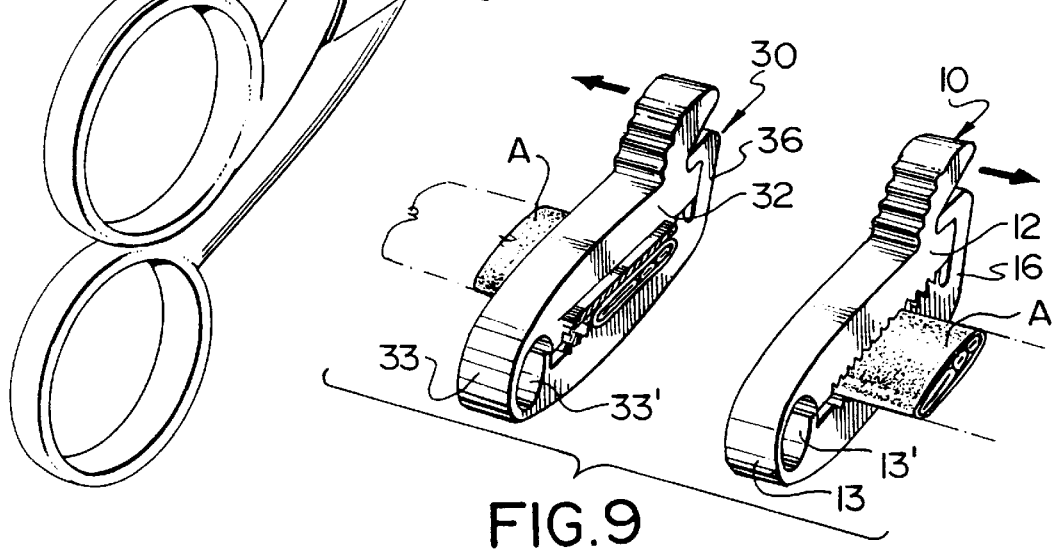

UMBILICAL CORD CLAMP

This application claims the benefit of provisional application Ser. No. 60/041,969, filed Mar. 27, 1997.

This invention relates to an unitary umbilical cord clamp.

BACKGROUND TO THE INVENTION

Severing of the umbilical cord is the oldest procedure and the most common surgical procedure. It happens to everyone at birth. Presently, the procedure is a three-step procedure comprising the steps of:

(a) fastening a first clamp on the umbilical cord;

(b) fastening a second clamp on the umbilical cord at a predetermined distance from the first one;

(c) cutting the cord in between the respective clamps with a pair of scissors.

This traditional procedure has substantial disadvantages which are summarized as follows; namely, the three-step procedure, above identified, takes a relatively long time, especially in instances of emergencies; there is a considerable amount of blood contained within the cord between the two clamps, thus, during cutting, the blood spurts out of the severed cord; if the blood is contaminated, for example, with either HIV or Hepatitis B, delivery personnel run the risk of infection; further two individual clamps must be used; and, each clamp as well as the scissors have to be individually sterilized before use.

SUMMARY OF THE INVENTION

The novel umbilical cord clamp according to the invention, has a parallel pair of U-shaped articulateable clamp members molded from a yieldable severable material such as nylon or other similar plastic. Each clamp member has a pair of distal arms with opposing clamping surfaces, preferably serrated, and proximate ends relatively interjoined by an articulating proximate arm that acts as a unitary and integral hinge for each clamp member. Each distal arm pair, along its laterally adjacent side margin with that of the other clamp member, is interjoined by a web sheet portion so as to constitute the clamp as a unitary pair of spatially disposed integral U-shaped clamp members which co-operatively close, forcing the webs onto the umbilical cord outer surface compressing the cord between the webs and the opposing clamping surfaces. The respective ends of the distal arms of each clamp member have a latch or interlocking means by which each distal arm end pair, relatively latches to lockingly close the unitary umbilical cord clamp. During closing of the umbilical cord clamp, the umbilical cord is first compressed by the interconnecting web members and also by inner opposite clamping surfaces of each U-shaped clamp member, driving out the blood therebetween or therein and thus, draining blood from that portion of the umbilical cord which is now confined between the webs. While this is happening between the inner portions of each opposite distal clamp arm surfaces of each U-shaped clamp pair also engage the outer perimeter of the umbilical cord, while constricting the inner vessels of the cord to close. The biasing forces of opposite distal inner arm surfaces further drains away any blood therebetween, to hold close the umbilical cord thereunder. Relative latching of the opposite distal arm ends, of each clamp member stabilizes close the clamp. After an appropriate interval, scissors are used to cut the webs and the umbilical cord confined between the web members; virtually no umbilical cord blood is released. After severing of the webs with the underling confined umbilical cord, the constant urging of opposite distal (serrated) inner surfaces of the distal arms hold close the severed ends of the umbilical cord until sealed by healing. If each distal arm pair defines parallel spatially disposed serrated surfaces the duration of time for the severed chord ends to heal closed can be reduced. After birth, the placenta, its cord and the attached single clamp member are discarded, while the other clamp member remains attached to the umbilical cord communicating to the infant until that cord withers and falls off or the clamp is released, or removed.

The above invention has advantage in that a single, yet compound clamp is used in a one-step clamping operation. Thereafter, the umbilical cord is cut with virtually no blood spurting out of the cord since the amount of blood, if any, remaining within is minimized; further, each U-shaped member is disposed from the other, by the interjoining web sheets positioned at a minimal distance not only to provide minimal spacing between each member for the scissors cut but to "force" out blood inside the underlying umbilical cord. The arrangement virtually eliminates chances of delivery personnel being contaminated by umbilical cord blood because virtually no blood erupts on severance by the scissors. The compound clamp can have particular advantages also for para-medical personnel who are out of hospital environment, requiring to service patients.

The invention therefore contemplates an unitary yet severable, surgical clamp, particularly suited for reducing blood contamination by draining and sealing closed an umbilical cord, and after umbilical cord severance, umbilical cord severed ends, comprising first, second and third clamp means, the second clamp means integral with and extending between and relatively spatially disposing the first and third clamp means, means for closing the surgical clamp, urging the second clamp means against the umbilical cord to force blood from within the umbilical cord away from a zone between said first and third clamp means and, locking the surgical clamp closed, whereupon severance of the second clamp means from the first and third clamp means also severs the umbilical cord therebetween, yet maintains sealingly closed at the one severed end of the umbilical cord. Particularly, the clamp is unitarially made from a yieldable severable material such as nylon or similar material. The first and third clamp members are U-shaped members with a flexible hinge along the proximate arm, and at distal ends of the distal arm are clamp means which close and lock each clamp member. The distal arms of each U-shaped clamp member is respectively interjoined by the second clamp means which is a web sheet between adjacent arms of first and third U-shaped members. The distal ends of the first and third U-shaped members have cam latch means which locks the clamp closed, preferably about an umbilical cord, thus allowing the web sheets to be cut as well as the underlining umbilical cord, severing the same and each remaining first and third clamp means is attached closing the severed umbilical cord.

BRIEF DESCRIPTION OF THE DRAWINGS

FIGS. 6 through 9 are perspective views showing the sequence of utilization of the clamp wherein;

FIG. 6 is a perspective view of the clamp during closure;

FIG. 7 is a perspective view of the clamp during closure, the open position being shown in phantom, the closed position being shown in solid; while FIG. 7A is an explanatory fragmentary side view of the clamp latching during closure;

FIG. 8 is a perspective of the clamp being severed by scissors (S), also severing the umbilical cord therein; and, FIG. 9 is a perspective of the severed clamp and umbilical cord whose distal severed ends are clamped closed.

THE PREFERRED EMBODIMENT

Figure 1:
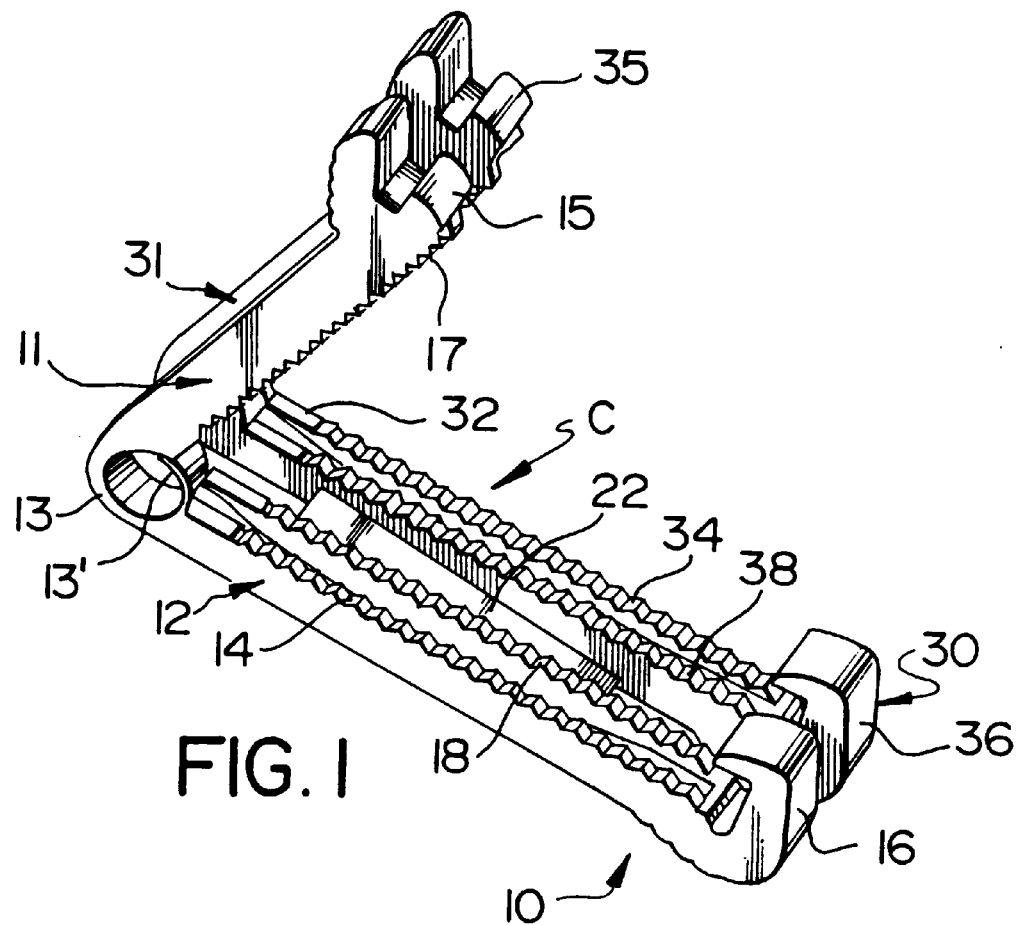
FIG. 1 is a perspective view of the novel clamp, according to the invention, in the open position.

Referring to FIG. 1, a unitary, yet severable, surgical clamp according to the invention, is generally shown as (C) and consists of a first, second and third clamp means respectively, (10), (20), and (30) molded from nylon or similar material so that it flexes or yields. In the preferred embodiment illustrated, the first and third clamp means (10,30) each is formed as an articulating U-shaped member comprising opposing pairs of clamp arms (11) and (12), on the one hand, and (31) and (32) on the other hand. Each are connected at their proximate ends with an integral proximate arm, respectively (13) and (33) so as to allow the U-shaped clamp member to close, as seen in FIGS. 2 and 6 through 9. In the side view, FIG. 2, the solid representation of the clamp (C) illustrates the flexing of the opposing arms (11,12) on closure about an umbilical cord (A); the phantom representation showing the clamp closed without an umbilical cord.

Extending between each adjacent clamping arm (11) and (31), is an integrally formed first web sheet (21) while a second web sheet (22) integrally extends between adjacent clamp arms (12) and (32). The two web sheets (21) and (22) constitute the second clamp means (20).

In order to lock closed the clamp (C), distal ends of opposing clamp arms (11,12); (31,32) have male and female cam latch elements, respectively (15) and (16) on the one hand, and (35) and (36) on the other hand. Extending along the inner surfaces of each clamp arm is an opposing clamp surface, which, in the preferred embodiment shown, is a parallel pair of serrated clamping surfaces along clamp arm (12), an outer serrated clamping surface (14) and inner serrated clamping surface (18); along clamp arm (11), outer serrated clamping surface (17) and inner serrated clamping surface (19); along clamp arm (32), outer serrated clamping surface (34) and inner serrated clamping surface (38); and along clamp arm (31), outer serrated clamping surface (37) and inner serrated clamping surface (39). The root plane of the outer serrated surfaces (14), (17), (34) and (37) are respectively disposed, when in the closed position, in parallel planes which are dimensioned apart from each other ($D_o$), which is a greater distance than the planes for the inner serrated surfaces (18,19) and (38,39), referenced ($D_i$); see FIGS. 4 and 5. Preferably, the second clamp means (20) has both of its web members (21) and (22) co-planar with, or as close as possible to the root plane of the adjacent inner serrations (19) and (39) in relation to the upper members and (18) and (38) in relation to the lower members—see FIG. 4. Hence, the web sheet (22) is co-planar with the root plane of the serrations (18) and (38) while the web sheet (21) is co-planar with the root plane of the serrations (19) and (39).

Figure 2:
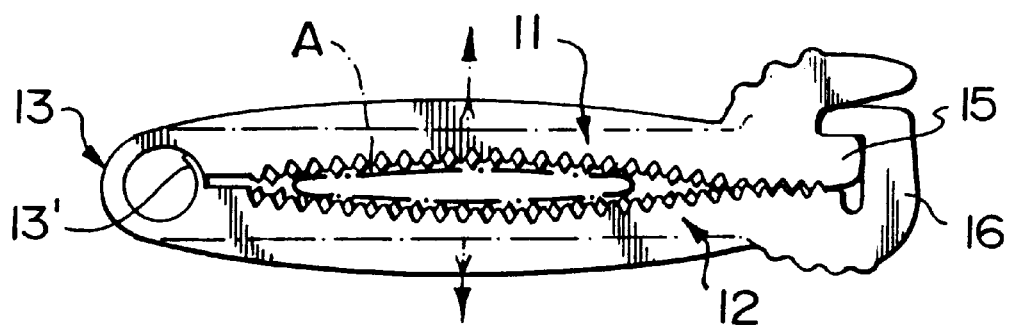
FIG. 2 is a side elevational view of the clamp in the closed position holding an umbilical cord; the phantom position thereof being the clamp closed but not holding any umbilical cord.
Figure 3:
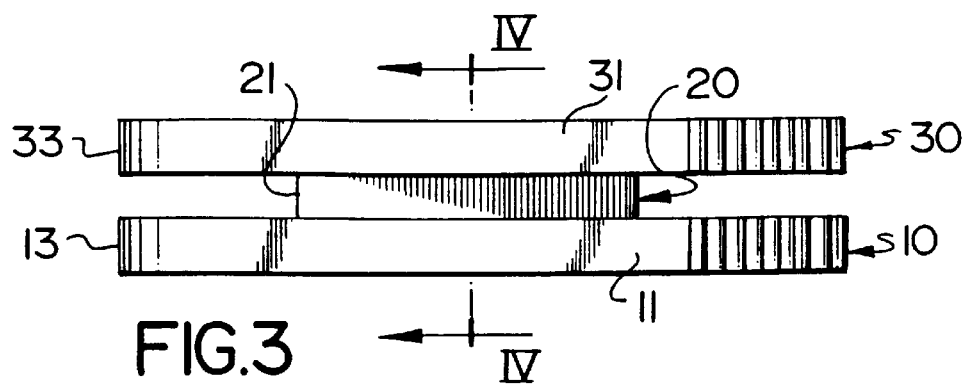
FIG. 3 is a top plan view of the clamp in the closed position.

In order to insure confinement of the umbilical cord (A) within the opposing clamp arms of each clamp member, at the hinges (13) and (33) respectively, the inner proximate portion has an arcuate hinge cover respectively (13') and (33'), as clearly seen in FIGS. 1, 2 and 9 which slidingly travels along the inner, upper surface of the respective arms (11) and (31), separating the hinge area from the opposing arm areas (11) and (12) on the one hand, and (31) and (32) on the other hand, so as to inhibit catching of the umbilical cord (A) in the hinge, as will be apparent hereafter.

Referring to FIGS. 6 through 9 and the operation of the clamp; on birth, the infant is voided from the womb with the umbilical cord attached to the infant on the one hand, and to the placenta still residing in the womb on the other hand.

Figure 6:
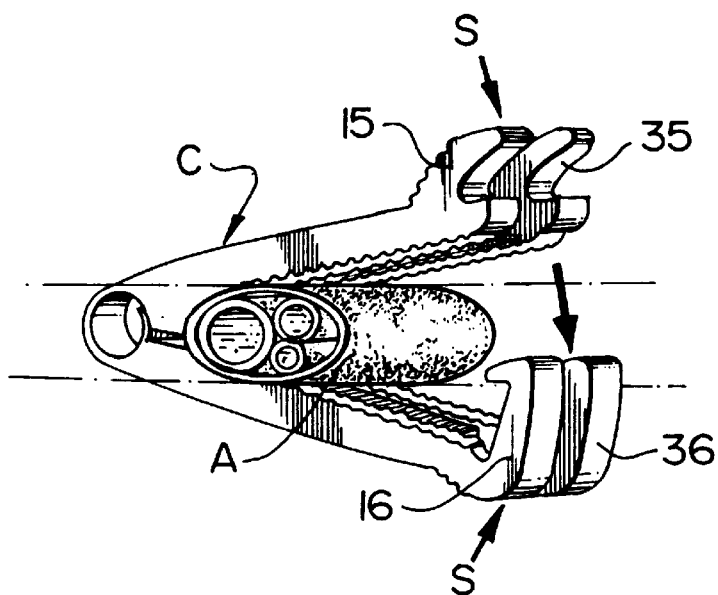

The clamp (C) is positioned as close as possible to the union of the umbilical cord with the infant, i.e., adjacent to the abdomen of the infant and the umbilical cord is clamped closed, as shown in FIGS. 6, 7 and 7A, by pushing the clamp members, arrows (S), into engagement. It is preferred, therefore, that the cam latch element (15,16 and 35,36) be resilient and hence, the whole clamp be integrally composed of nylon or similar material. During closure, FIGS. 7 and 7A, the male latch element (16) moves in the direction of the arrow (L) in FIGS. 7 and 7A during closure. This is accommodated by the thumb and index fingers being placed at opposite arrows (S) on each clamp member (10,30). The clamp latches close because the male latch elements (16) and (36) flex in the direction of arrow (L) and then snap into engagement following a cam action along the face of the female elements (15,35). On engagement of the clamp distal ends (15) and (16) on the one hand, and (35) and (36) on the other hand, latch into the configuration shown in the perspective FIG. 7.

Figure 4:
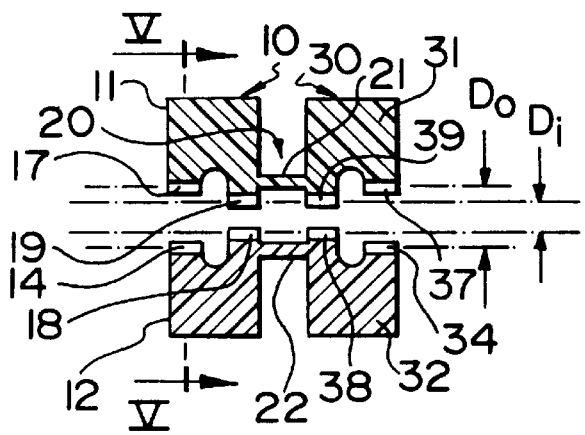
FIG. 4 is a section along lines IV—IV of FIG. 3.
Figure 5:
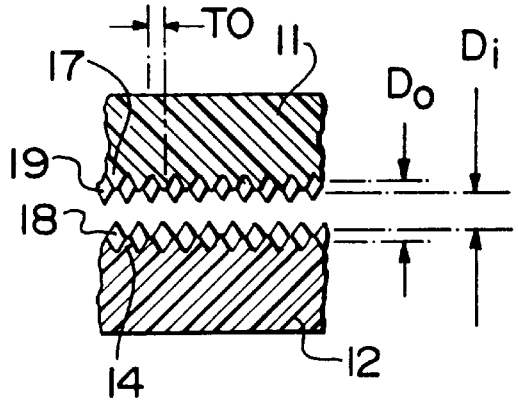
FIG. 5 is a section along lines V—V of FIG. 4.

The clamp (C) closing and latching procedure is now described as a continuous sequential sequence and with reference to FIG. 4. Closure of the clamp commences by applying opposite forces (F), as by index finger and thumb, to the clamp (C) distal ends, as shown. Firstly, the two webs (21) and (22) oppositely engage the outside of the umbilical cord (A). Because each of the webs are parallel to and preferably co-planar to the root plane of opposite interior serrated surfaces (18,19) and (38,39), respectively, blood is forced further out of the vessels and the artery of the umbilical cord (A) in opposite directions. Secondly, at the same time, the opposite inner serrated surfaces (18, 19) and, (38,39), respectively engage the outer surround of the umbilical cord (A) initially allowing blood passage from between the web regions (21,22), which are now being juxtaposed onto the outside surface of the umbilical cord (A). Thirdly, because the root plane of the outer serrated surfaces (14,17) and, (34,37) are relatively further disposed at a dimension ($D_o$) than those of the inner pair of serrated surfaces, respectively, (18,19) and (38,39) at dimension ($D_i$), the transition between these two dimensions ($D_o$) and ($D_i$) forces blood less out of the artery and the two vessels of the umbilical cord (A), bounded between inner and outer serrated clamping surfaces encouraging chord healing between the inner and outer clamping surfaces of each clamp, thus reducing healing time for the sealing the severed ends of the cord (A).

The webs (21) and (22) respectively are broad enough so as to allow a pair of scissors (S'), and now referring to FIG. 8, to extend therebetween. When the scissors (S') are closed, there is severing not only the web sheets (21) and (22) but also of the underlying umbilical cord (A). On severance, each clamp (10) and (30) seals closed its underlying severed umbilical cord end, as shown in FIG. 9. It is desired that the web sheets (21) and (22) respectively lay co-planar in or as close as possible to the root plane of the inner serrated surfaces, for web (21), co-incident to the root plane (19–39) and for web (22), co-incident to the root plane (18–38). This encourages good cord blood drainage. In order to encourage good cord sealing, it is preferred that there be inner (18,19; 38,39) and outer (14,17;34,35) pairs of parallel clamping surfaces, each preferably serrated. It is further preferred, and now referring to the cross-sectional FIG. 5, that the outer teeth (14), (17) are offset by dimension (TO) from the inner teeth (18) and (19); similarly, for the clamp (30). This assists to increase clamp engaging forces on the umbilical cord, during clamping, and additional drainage of the blood from beneath the clamp (C).

When the placenta is voided by the mother, the placenta and one of the clamp members, clamping closed the severed end of the umbilical cord may be discarded with the placenta. The other clamp members remains on the infant umbilical cord. After treating in the conventional fashion, the umbilical cord falls off the infant and the clamp and withered cord discarded or alternatively, the clamp may be removed by cutting the hinge or separating the latched lock (15,16 or 35,36).

We claim:

1. A unitary, yet severable, surgical clamp, particularly suited for reducing blood contamination and for draining and sealing closed an umbilical cord, and after umbilical severance, umbilical severed ends, comprising:
   (a) first, second and third clamp means, the second clamp means integral with and extending between and relatively spatially disposing the first and third clamp means;
   (b) means for closing the surgical clamp;
   (c) means for urging the second clamp means against the umbilical cord to force blood away from within the umbilical cord from a zone between said first and third clamp means;
   (d) means for locking the surgical clamp closed, whereupon severance of the second clamp means from the first and third clamp means also severs the umbilical cord therebetween.

2. The clamp as claimed in claim 1 wherein the means for locking lockingly seals closed both severed ends of the umbilical cord.

3. The clamp as claimed in claim 1 wherein there is an integral discrete latch means for each of the first and third clamp means.

4. A unitary, yet severable, surgical clamp, particularly suited for reducing blood contamination and for draining and sealing closed an umbilical cord, and after umbilical severance, umbilical severed ends, comprising:
   (a) first and third clamp members, each with their own pair of clamp arms, each defining opposing clamping surfaces;
   (b) severable web means, being a second clamp member, integrally extending between adjacent clamp arms of each clamp member in a plane proximate to the opposing clamp surfaces;
   (c) means for constraining the clamp closed during which the web means firstly are juxtaposed into urging engagement on the perimeter of an umbilical cord, draining away blood therebetween, while opposing arms of each clamp member, then engagingly seal closed fluid conveying channels within the umbilical cord.

5. The clamp as claimed in claim 4, wherein the clamp surfaces define an adjacent parallel pair of inner and outer clamping surfaces.

6. The clamp as claimed in claim 4, wherein the clamp surfaces define inner and outer clamping surfaces, the inner clamping surfaces disposed relatively closer to each other than the outer clamping surfaces.

7. The clamp as claimed in claim 4, wherein the opposing clamp surfaces are serrated.

8. The clamp as claimed in claim 5, wherein the opposing clamp surfaces do not fully mesh.

9. The clamp as claimed in claim 5, wherein the clamp surfaces define adjacent inner and outer clamping surfaces with the two opposing inner clamping surfaces of each clamp disposed relatively closer to each other than the opposing outer clamping surfaces of each clamp, and with opposing serrated clamping surfaces not fully meshing when the clamp is closed.

10. The clamp as claimed in claim 5, wherein each serrated surface has a root plane and the web means are approximately co-planar to the root plane.

11. The clamp as claimed in claim 10, wherein the clamp surfaces define adjacent inner and outer clamping surfaces with the two opposing inner clamping surfaces of each clamp disposed relatively closer to each other than the opposing outer clamping surfaces of each clamp, the opposing serrated clamping surfaces not fully meshing, the web means approximately co-planar with a prolongation of the root planes and extending between adjacent inner serrated clamping surfaces.

12. The clamp as claimed in claim 10, wherein the clamp surfaces define adjacent inner and outer clamping surfaces with the two opposing inner clamping surfaces of each clamp disposed relatively closer to each other than the opposing outer clamping surfaces of each clamp, the opposing serrated clamping surfaces not fully meshing, the web means approximately co-planar with a prolongation of the root planes and extending between adjacent inner serrated clamping surfaces, each serrated clamping surface having teeth which as between adjacent inner and outer clamping surfaces are not in alignment.

13. A unitary, yet severable, surgical clamp, particularly suited for reducing blood contamination and for draining and sealing closed an umbilical cord, and after umbilical severance, umbilical severed ends, comprising:
   (a) first and third clamp members each with their own pair of clamp arms, each defining opposing clamping surfaces;
   (b) severable web means, being a second clamp member, integrally extending between adjacent clamp arms of each clamp member in a plane proximate to the opposing clamp surfaces;
   (c) means for constraining the clamp closed during which the web means firstly are juxtaposed into urging engagement on the perimeter of an umbilical cord, draining away blood therebetween, while opposing arms of each clamp member, then engagingly seal closed fluid conveying channels within the umbilical cord;
   wherein said clamp is composed of nylon.

14. The clamp as claimed in claim 13, wherein said clamp surfaces define inner and outer clamping surfaces, the inner surfaces disposed relatively closer to each other than the outer clamping surfaces.

15. The clamp as claimed in claim 13, wherein said clamp surfaces define an adjacent parallel pair of inner and outer clamping surfaces.

16. The clamp as claimed in claim 13, wherein the opposing clamp surfaces are serrated.

17. The clamp as claimed in claim 16, wherein each of said clamp surfaces define adjacent inner and outer clamping surfaces with the two opposing inner clamping surfaces of each clamp disposed relatively closer to each other than the opposing outer clamping surfaces of each clamp, and with opposing serrated clamping surfaces not fully meshing when the clamp is closed.

18. The clamp as claimed in claim 16, wherein each serrated surface has a root plane and the webs are approximately co-planar to the root plane.

19. The clamp as claimed in claim 15, wherein said clamp surfaces define adjacent inner and outer clamping surfaces, the opposing inner clamping surfaces disposed relatively closer to the other pair than those of the opposing outer clamping surfaces, with opposing serrated clamping surfaces not fully meshing, the web means approximately co-planar with a prolongation of the root planes and extending between adjacent inner serrated clamping surfaces.

20. The clamp as claimed in claim 15, wherein said clamp surfaces define adjacent inner and outer clamping surfaces, the opposing inner clamping surfaces disposed relatively closer to the other pair than those of the opposing outer clamping surfaces, with opposing serrated clamping surfaces not fully meshing, the web means approximately co-planar with a prolongation of the root planes and extending between adjacent inner serrated clamping surfaces, each serrated clamping surface having teeth which as between adjacent inner and outer clamping surfaces are not in alignment.

* * * * *